United States Patent
Bucholz et al.

(10) Patent No.: US 6,928,490 B1
(45) Date of Patent: Aug. 9, 2005

(54) NETWORKING INFRASTRUCTURE FOR AN OPERATING ROOM

(75) Inventors: Richard D. Bucholz, St. Louis, MO (US); Leslie McDurmont, Ballwin, MO (US)

(73) Assignee: St. Louis University, St. Louis, MO (US)

( * ) Notice: Subject to any disclaimer, the term of this patent is extended or adjusted under 35 U.S.C. 154(b) by 0 days.

(21) Appl. No.: 09/573,228

(22) Filed: May 19, 2000

Related U.S. Application Data

(60) Provisional application No. 60/135,057, filed on May 20, 1999.

(51) Int. Cl.[7] .............................................. G06F 15/16
(52) U.S. Cl. ....................... 709/249; 709/208; 709/218; 700/3; 700/4; 700/9; 700/17; 700/19; 700/20; 700/247; 340/3.1; 340/3.9; 340/310.01; 606/1
(58) Field of Search .............................. 700/2–4, 9, 17, 700/19, 20, 65, 83, 247–249; 709/208, 218, 249; 340/3.1, 3.9, 310.01, 825.29, 310.02; 370/450; 606/1, 2

(56) References Cited

U.S. PATENT DOCUMENTS

| | | | |
|---|---|---|---|
| 4,644,582 A | 2/1987 | Morishita et al. ............... 382/6 |
| 4,722,056 A | 1/1988 | Roberts et al. .............. 364/413 |
| 4,815,106 A * | 3/1989 | Propp et al. ................. 375/257 |
| 4,879,668 A | 11/1989 | Cline et al. .................. 364/522 |
| 4,958,283 A | 9/1990 | Tawara et al. .......... 364/413.13 |
| 4,987,412 A | 1/1991 | Vaitekunas et al. .......... 340/721 |
| 5,005,126 A | 4/1991 | Haskin .................. 364/413.13 |
| 5,027,422 A | 6/1991 | Peregrim et al. ............. 382/48 |
| 5,048,103 A | 9/1991 | Leclerc et al. ................ 382/44 |
| 5,051,720 A * | 9/1991 | Kittirutsunetorn ..... 340/310.02 |
| 5,099,846 A | 3/1992 | Hardy .................... 128/653.13 |
| 5,241,472 A | 8/1993 | Gur et al. .............. 364/413.22 |
| 5,261,404 A | 11/1993 | Mick et al. ............... 128/653.1 |
| 5,272,625 A | 12/1993 | Nishihara et al. ....... 364/413.13 |
| 5,274,551 A | 12/1993 | Corby, Jr. .............. 364/413.13 |
| 5,284,142 A | 2/1994 | Goble et al. ............. 128/653.1 |

(Continued)

FOREIGN PATENT DOCUMENTS

| | | |
|---|---|---|
| EP | 0 833 266 A2 | 4/1998 |
| EP | 0 890 919 A1 | 1/1999 |
| WO | WO 94/24933 | 11/1994 |
| WO | WO 96/11624 | 4/1996 |

OTHER PUBLICATIONS

Sun™ web page for Jini connection technology, http://www.sun.com/jini, dated May 19, 1999.

(Continued)

*Primary Examiner*—Anthony Knight
*Assistant Examiner*—Crystal J Barnes
(74) *Attorney, Agent, or Firm*—Senniger Powers

(57) ABSTRACT

A networking infrastructure for an operating room, comprising a plurality of medical devices, each device of which is connected through a single communication channel to the network, wherein each device may be controlled through a local interface, or through a remote interface available through the network. Furthermore, the networking infrastructure operates in robust manner with respect to the removal of a communication channel to the network associated with the removal of medical device from the network, or with respect to the addition of a communication channel to the network associated with the addition of a medical device to the network.

21 Claims, 5 Drawing Sheets

U.S. PATENT DOCUMENTS

| | | | | |
|---|---|---|---|---|
| 5,291,401 | A | | 3/1994 | Robinson .................. 364/413.13 |
| 5,309,356 | A | | 5/1994 | Nishide et al. ......... 364/413.19 |
| 5,353,220 | A | | 10/1994 | Ito et al. .................. 364/413.13 |
| 5,383,454 | A | | 1/1995 | Bucholz .................... 128/653.1 |
| 5,402,337 | A | | 3/1995 | Nishide .................... 364/413.13 |
| 5,465,378 | A | | 11/1995 | Duensing et al. ............ 395/800 |
| 5,483,606 | A | | 1/1996 | Denber ......................... 382/294 |
| 5,490,221 | A | | 2/1996 | Ransford et al. ............ 382/130 |
| 5,531,227 | A | | 7/1996 | Schneider .................. 128/653.1 |
| 5,531,520 | A | | 7/1996 | Grimson et al. ............. 382/131 |
| 5,568,384 | A | | 10/1996 | Robb et al. .............. 364/419.13 |
| 5,581,638 | A | | 12/1996 | Givens et al. ............... 382/294 |
| 5,615,112 | A | | 3/1997 | Liu Sheng et al. .......... 395/615 |
| 5,631,844 | A | | 5/1997 | Margrey et al. ............. 364/496 |
| 5,633,951 | A | | 5/1997 | Moshfeghi .................... 382/154 |
| 5,659,792 | A | | 8/1997 | Walmsley .................... 395/807 |
| 5,682,526 | A | | 10/1997 | Smokoff et al. ............. 396/615 |
| 5,704,371 | A | | 1/1998 | Shepard ....................... 128/897 |
| 5,734,915 | A | | 3/1998 | Roewer ........................ 395/773 |
| 5,740,428 | A | | 4/1998 | Mortimore et al. .......... 395/615 |
| 5,788,688 | A | | 8/1998 | Bauer et al. |
| 5,819,229 | A | | 10/1998 | Boppe |
| 5,826,102 | A | | 10/1998 | Escobar et al. .............. 395/806 |
| 5,884,298 | A | | 3/1999 | Smith, II et al. ................ 707/2 |
| 5,915,250 | A | | 6/1999 | Jain et al. ..................... 707/100 |
| 5,970,499 | A | | 10/1999 | Smith et al. ................. 707/104 |
| 5,997,476 | A | | 12/1999 | Brown ......................... 600/300 |
| 5,997,528 | A | | 12/1999 | Bisch et al. ..................... 606/1 |
| 5,999,840 | A | | 12/1999 | Grimson et al. ............. 600/424 |
| 6,003,007 | A | | 12/1999 | DiRienzo ......................... 705/4 |
| 6,117,127 | A | * | 9/2000 | Helmreich et al. .............. 606/1 |
| 6,405,261 | B1 | * | 6/2002 | Gaucher ....................... 709/250 |
| 6,466,971 | B1 | * | 10/2002 | Humpleman et al. ....... 709/220 |
| 6,661,784 | B1 | * | 12/2003 | Nykanen ...................... 370/338 |
| 6,671,563 | B1 | * | 12/2003 | Engelson et al. ............... 700/2 |
| 6,783,523 | B2 | * | 8/2004 | Qin et al. ........................ 606/1 |
| 2001/0037366 | A1 | * | 11/2001 | Webb et al. |
| 2004/0158193 | A1 | * | 8/2004 | Bui et al. |

OTHER PUBLICATIONS

Jini™ Distributed Event Specification–1.0, dated Jan. 25, 1999.

Jini™ Architecture Specification–1.0, dated Jan. 25, 1999.

Jini™ Lookup Service Specification–1.0, dated Jan. 25, 1999.

Jini™ Device Architecture Specification–1.0, dated Jan. 25, 1999.

Christensen et al., "Individualizing Neuro–anatomical Atlases Using a Massively Parallel Computer," IEEE, Jan. 1996, pps. 32–38.

Galvin, Jeffrey R. et al., "Imaging Corner, The Virtual Hospital, Providing Multimedia Decision Support Tools via the Internet," 1995, SPINE, vol. 20, No. 15, pp. 1735–1738.

Davis et al., "Three–Dimensional High–Resolution Volume Rendering (HRVR) of Computed Tomography Data: Applications to Otolaryngology—Head and Neck Surgery," Laryngoscope, vol. 101, Jun. 1991, pp. 573–582.

Rosenman et al., "Vistanet: Interactive Real–Time Calculation and Display of 3–Dimensional Radiation Dose: An Application of Gigabit Networking," Int'l J. Radiation Oncology Biol. Phys., vol. 25, Jan. 1993, pp. 123–129.

Heinz et al., "Examination of the Extracranial Carotid Bifurcation by Thin–Section Dynamic CT: Direct Visualization of Intimal Atheroma in Man (Part 1)," American Journal of Neuroradiology, Jul./Aug. 1984, pp. 355–359.

Hatch, "Reference–Display System for the Integration of CT Scanning and the Operating Microscope," Master of Engineering Thesis, Dartmouth College, Hanover, NH, Oct. 1984.

Pelizzari, Charles A., "Accurate Three Dimensional Registration of CT, PET, and/or MR Images of the Brain," J. of Computer Assisted Tomography, vol. 13, No. 1, pp. 20–26 (Jan.–Feb. 1989).

Gramkow, Claus, "Registration of 2D and 3D Medical Images," Lyngby, IMM–EKS–1996–1 (Jan. 1996).

Perry et al., "Emission and Transmission Spect Data Combination in Interactive 3D Image Presentation," The Journal of Nuclear Medicine, May 1989, p. 835, Abstract No. 443.

Tsui et al., "Three–Dimensional Display Methods for Image Data Obtained with Spect," European Journal of Nuclear Medicine, Aug. 1989, p. 558, Abstract No. 639.

Penn et al., "Stereotactic Surgery with Image Processing of Computerized Tomographic Scans," Neurosurgery, vol. 3, No. 2, 1978, p. 157–163.

Rosenman et al., "Three–Dimensional Display Techniques in Radiation Therapy Treatment Planning," Int'l Radiation Oncology Biol. Phys., vol. 16, Jan. 1989, pp. 263–269.

Antonakopoulos, T., "A Spectrum Reuse/Token Passing (SRTP) Protocol for Communications in the Factory Environment Over the Power Grid," ISIE, Proceedings of the IEEE International Symposium on Industrial Electronics, Athens, Greece, Jul. 10–14, 1995, pp. 878–883, vol. 2, XP002172552, New York, New York.

PCT International Search Report Issued Application No. WO00/72180.

* cited by examiner

NETWORKING INFRASTRUCTURE FOR AN OPERATING ROOM

This application claims benefit of Provisional Application No. 60/135,057 filed May 20, 1999, from the priority is claimed.

I. BACKGROUND OF THE INVENTION

I.A. Field of the Invention

The present invention relates to an electronic infrastructure for an operating room. More particularly, the present invention relates to a simplified infrastructure for an operating room that allows control of highly complex devices and provides for communication among devices.

I.B. Description of Related Art

A modern surgical operating room can be viewed as either the pinnacle of technological development or an example of shortcomings of modern technology. Within the operating room surgeons must perform increasingly complex procedures through progressively smaller openings in their patient's bodies while incurring the lowest possible incidence of complications and side effects. The exponential growth of medical knowledge and the rapid development and deployment of new therapeutic technologies intensify these demands. These developments constitute a constantly changing standard of care in the treatment of specific conditions from which the surgeon must rapidly choose the optimal care for a given patient during a surgical procedure. These decisions must be made within the financial context of a typical hospital experiencing tighter fiscal restraints and managed and staffed by employees experiencing rapid turnovers. In such a financial context, an experienced surgeon supported by experienced technicians is a rare combination.

Within this environment, consider the expectations of both the patient and society of the process that occurs within the operating room. A patient with a complex disease undergoes surgery in a setting that consumes financial resources at an unprecedented rate than can be higher than many complex manufacturing processes. The surgical process places a human life at risk using technologically complex devices, but with the expectation that the patient will emerge substantially unchanged except for the correction of the disorder for which the patent is being treated. After treatment, the patient is wheeled out of the operating room and another patient, usually with a completely different but equally demanding condition, is brought in to undergo a completely different procedure which may have little similarity in the procedure just performed. This process is repeated throughout the day with minimal time between each case and with each patient expecting optimal quality and results from the complex procedures.

An industrial analogy for the operating room could be a factory optimized to produce a complex computer and then, within a few minutes, changed completely to produce an automobile. This production facility would have extremely low tolerance for any error, employ a constantly changing non-technical work force, and operate on an imperative to minimize the time required to produce goods and to change production modes. The analogy can be extended further by noting that the manufacturing process to produce either the computer or automobile could change weekly due to technical innovations in both products. Finally, the exact form of the computer or car produced changes with each and every unit manufactured, as no two computers or cars in the medical analogy are exactly alike.

The pace of technical innovation promises to change not only which surgical procedures are performed, but also how the procedures are carried out. The imperative to improve patient care will compel the surgeon to employ increasingly complex devices, each of which have profound effects upon the nature of the surgical process. An example of technology deployment is the operative MRI scanner, in which the entire surgical process must be performed in the hostile environment of a strong magnetic field. Few industrial processes could accommodate such a drastic change in their production facility.

The individual in charge of this process, the surgeon, is also changing in response to external demands. Surgeons are experiencing increasing pressure to reduce the cost of their interventions and maximize the number of patients they see. The result is that they often do not have sufficient time to familiarize themselves with either complex surgical devices or the specific anatomy of the patient, or to keep up with every change in medical therapeutics as it occurs. Even trying to control complex devices during surgery can be challenging, given the sterile work environment of the surgeon. For example, many electronic devices do not tolerate sterilization, and foot switches are commonly employed to control surgical devices. This may lead to a phalanx of foot pedals on the floor to control a number of complex devices. Finally, surgical experience dealing with a specific disease process is dissipating. In order to control costs and to support their income, surgeons are under pressure not to refer patients with complex medical problems away to experts. The result is that surgeons with less expertise, time, and experience may be treating complex surgical conditions. This produces a need to assist the surgeon with control of multiple complex surgical devices in the operating room, and to present the surgeon with information critical for success in rendering operative decisions. This information may include the assistance of a surgical consultant who may need control of the devices within the operating room even though the consultant is located at a distance from the actual operation.

II. SUMMARY OF THE INVENTION

To overcome the disadvantages of the prior systems and methods, and in accordance with the purposes of the invention, as embodied and broadly described herein, there is provided a networking infrastructure for an operating room.

Additional features and advantages of the invention will be set forth in the description that follows, and in part will be apparent from the description, or may be learned from the practice of the invention. The objectives and other advantages of the invention will be realized and attained by the apparatus and methods particularly pointed out in the written description and claims herein as well as the appended drawings.

III. BRIEF DESCRIPTION OF THE DRAWINGS

The accompanying drawings, which are incorporated in and constitute part of the specification, illustrate a presently preferred embodiment of the invention and together with the general description given above and detailed description of the preferred embodiment given below, serve to explain the principles of the invention.

IV. DESCRIPTION OF THE PREFERRED EMBODIMENTS

Figure 1:
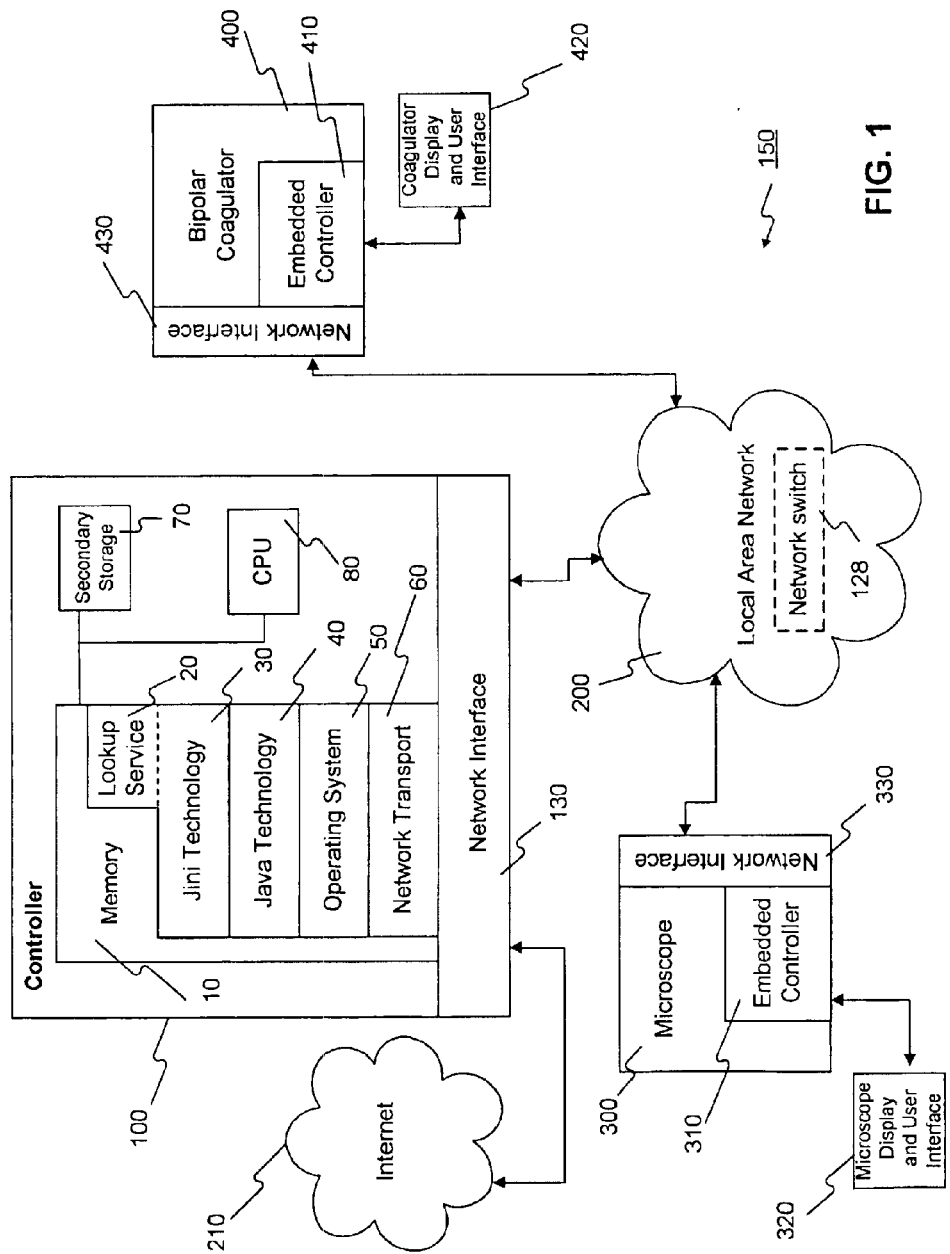
FIG. 1 is a schematic diagram illustrating a first embodiment of the present invention operating in conjunction with a bipolar coagulator and a microscope.

Reference now will be made in detail in the present embodiments of the invention as illustrated in the accompanying drawings. Whenever possible, the same reference number will be used throughout the drawings and the following description to refer to the same or like parts.

The network infrastructure of the present invention provides information to the surgeon and allows the surgeon to control complex surgical devices with a user-friendly interface. Presently, computer-type networks are not routinely employed in operating rooms. Surgical instruments and their respective controllers are typically proprietary devices with minimal provision for interactivity with other devices. As a result, there is limited, if any, communication between devices. The small degree of communication that is available is achieved by using dedicated cables, each of which must be connected properly to the communicating devices in accordance with surgical objectives. For example, a surgical microscope is connected to a video monitor using a video cable, a navigational device using a serial cable for robotic control, and connected to a foot switch with a specially manufactured cable to allow surgeon control. A fourth cable can be used if the device is to be tracked by the navigational system for robotic control, and other video cables are needed if the microscope is to display video output of the navigational device for a heads up display. Hence, simply using one device, such as the microscope, may require five cables and ten connections, each of which may be specific for a given device. These connections may have to be made during the course of surgery if the device is shared between different operations or if the device is unavailable at the beginning of an operation.

The result in some cases is a network of devices, each connected to other devices by a plurality of cables strewn about on the operating room floor which must be connected properly to work. Such a system has little fault tolerance. Since the operating room staff, with its high turnover rate, is typically minimally educated about how to maintain and connect all these cables and, since each cable has a unique function, damage to the cables is likely. Replacement of some cables may be difficult as they are proprietary. The breakage of a single pin in a single connector can result in the unavailability or improper operation of a piece of equipment and, even worse, a malfunction during a procedure. Reliance on operative connections between complex surgical devices can increase if image-guided devices employ other features. The need for communication and tight control between surgical devices will only increase over time.

As stated above, the network infrastructure of the present invention not only allows control of surgical devices but preferably allows information delivery to the surgeon as well. In particular, the Internet is burgeoning with medical information that may be useful to a surgeon during the course of a complex procedure. For example, on-line databases are being developed which provide statistics about success for a particular intervention refined by anatomy, histology, and patient characteristics. This information could be vitally important to a surgeon managing a rare condition for which the surgeon may have little experience. Development of these databases has been fueled by concerns about the cost of medical care. In fact, with the wealth of medical information currently on the internet, the concern is not that there is insufficient information, but rather too much information, which could flood and distract the surgeon from the task at hand. Therefore, the surgeon must closely control the content and timing of information received and used to carry out the procedure just as the surgeon must control the operating instruments employed during the procedure.

Just as the Internet could be used to deliver information into the operating room environment, it could be used to convey information out of the operating room environment to experienced surgical consultants. The network infrastructure of the present invention allows close control over this information leaving the operating room. Patient privacy and confidentiality is of paramount importance, and an operating room network should not "leak" information of any sort to the Internet. Further, the network infrastructure of the present invention controls devices within the operating room, while ensuring that the operating devices are not accidentally controlled from outside the operating room unless specifically granted authorization by the local surgeon. The present invention contemplates transmission of specific information in certain situations, such as in teaching institutions and procedures performed with the assistance of a remote expert, where transmission of information out of the operating room will be extremely important to the quality of the expert's consultation. Individuals within the operating room, consisting of the medical team directly responsible for all aspects of the patient's care, control whether or not information is actually transferred out of the operating room. Further, control of devices with the operating room can be conveyed by the local team to the remote consultants if desired.

To accomplish the above functionality, an embodiment of the present invention closely connects the devices within the operating room using a particular protocol and cabling while selectively communicating bidirectionally with the world beyond the operating room. Since many devices in the operating room can generate large data streams (such as video), one implementation of the present invention utilizes a broadband network within the operating room. Since this implementation of the network infrastructure of the present invention must be capable of controlling devices such as robots which demand accurate timing, the network within each operating room must be isolated from stray network traffic that could interfere with communications within a given operating theater. Such isolation is offered by the current invention.

Networks, as usually conceived, tend to be static constructs, such as desktop computers connected within an office network. This is in direct distinction to the dynamic nature of an operating room. Rather than consisting of a number of devices which stay connected for long periods, the operating room is continually in flux. Surgical devices may be present for only a portion of a particular procedure, with the preferences of the surgeon, the demands of the procedure, and the availability of specific devices dictating what will be present in the operating room for any given procedure. Therefore, the present invention contemplates simplified physical connections wherein the device initiates communication automatically and promptly to the network upon physical connection. In addition, the operating system (s) of the present invention allow disconnection and re-connection without any penalty or delay. Since the systems are, in many instances, life support devices, the present invention contemplates that the components of the system are capable of continuous operation and local control despite connection or disconnection of a particular device from the network or failure of the entire network. The intervention allows and actively facilities operation and control of every device locally whether networked or not. In short, the physical connections and network programs are robust and highly fault tolerant.

One implementation of the present invention preferably employs the Jini networking protocol (as developed by Sun Microsystems), herein incorporated by reference. The Jini network protocol allows a Jini compatible device to make and break network connections instantaneously upon physical connection and disconnection of the device to the network. Further, communications establish in a Jini compatible network allow prompt sharing of information between, and control of, devices after connection. The control of networked devices is orchestrated through standard Internet and web technology such as the hypertext transfer protocol (e.g., http over TCP/IP).

FIG. 1 depicts exemplary first networking infrastructure 150 in a first embodiment of the present invention. First networking infrastructure 150 comprises various components, including both hardware and software. First networking infrastructure 150 includes local area network 200 and controller 100. Local area network 200 further includes a plurality of exemplary devices, such as microscope 300, bipolar coagulator 400, as well as network switch 128. Local area network 200 may further include a plurality of additional devices pertinent to a given operating room. Further still, first networking infrastructure 150 may include 210. One skilled in the art should appreciate the Internet 210, as depicted in FIG. 1, may comprise a subset of the network conventionally known as the "Internet," such as, for example, a wide area network, a hospital Intranet, or University Intranet secured behind a network firewall. Controller 100 further includes both hardware and software components, including CPU 80, memory 10, such as RAM, secondary storage 70, and network interface 130. In a preferred embodiment of the present invention, memory 10 may include Jini technology 30, Java technology 40, lookup service 20, operating system 50, and network transport 60.

Each of the plurality of devices in first networking infrastructure 150 contains a corresponding network interface, an embedded controller, and is connected to a corresponding local display and user interface. For example, microscopic 300 contains embedded controller 310, network interface 330, and display and user interface 320.

The suitability of the Jini networking protocol, functioning between the embedded controllers of the plurality of devices and controller 100, is made more apparent when the inherent organization of the operating room is taken into account. Hospitals typically have operating suites with a number of separate operating rooms, each with almost complete autonomy. The current invention dictates that a local area network be established within each operating room to allow control and information flow within each room. Controller 100 may be further equipped with two network connections on network interface 130 to allow linkage and selective bidirectional communications between the operating room local area network 200 and Internet 210. Therefore, according to one implementation of the present invention, selective bidirectional communication with Internet 210 is enabled by operating system 50 of controller 100.

Each operating room would have network switch 128 located either in the operating room or physically part of controller 100. Network switch 128 allows devices in the operating room to communicate to the controller 100 with a dedicated broad bandwidth connection, and extraneous Internet network traffic is selectively prevented from entering the room's network through controller 100. Thus, the surgeon can exercise control of devices within the operating room with a relatively fast response time and secure patient information, while gaining access to Internet 210. Further, selective control of any device can be shared with another controller on Internet 210 as designated by the local system.

IV. A. Architecture

Figure 2:
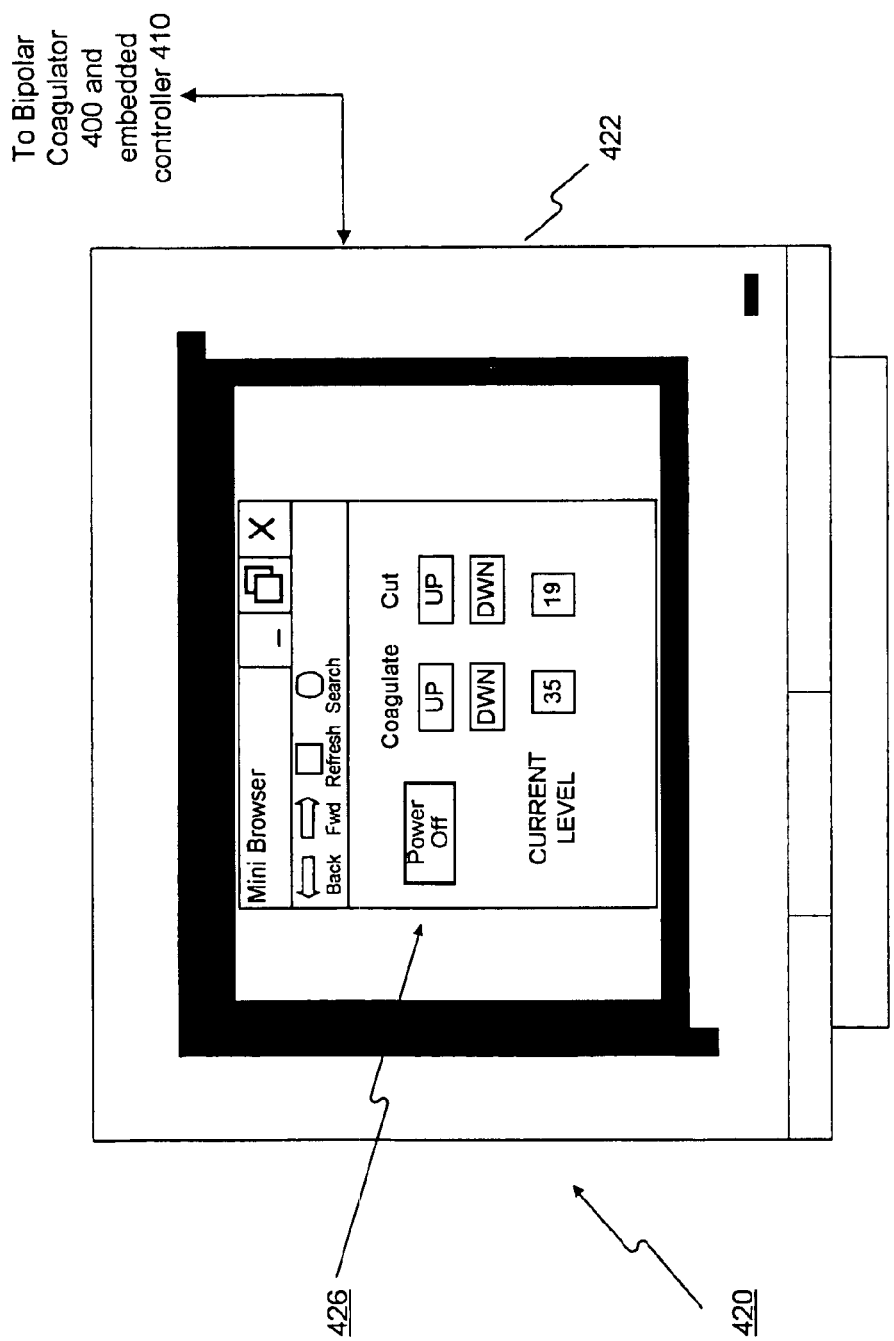
FIG. 2 is a detailed view of an exemplary display and user interface associated with the bipolar coagulator of FIG. 1.

According to one embodiment of the present invention, as illustrated in FIG. 1, each networked device in the operating room has an embedded controller that is Jini-compliant and capable of communication using standard Jini communication protocols over local-area network 200 and, through controller 100, Internet 210. For example, bipolar coagulator 400 includes embedded controller 410, and microscope 300 includes embedded controller 310. Each device is controlled locally using its own embedded controller that drives a display and user interface device. As illustrated in FIG. 1, bipolar coagulator 400 is modified by the addition of embedded controller 410 that interfaces with local area network 200 through network interface 430, and also interfaces with display and user interface 420. A more detailed view of display and user interface 420 is depicted in FIG. 2, and includes a touch-sensitive flat panel 422. As depicted in FIG. 2, embedded controller 410 has software for a "minibrowser" 426 (a scaled-down browser) stored in read-only (ROM) along with control forms specific for the device written in the html language. The control forms are displayed on touch sensitive flat panel display 422 upon startup of bipolar coagulator 400, and incorporates virtual buttons that are actuated by touch. When a user touches a button to request a desired task, minibrowser 426 activates embedded controller 410 through an interface so that embedded controller 410 controls bipolar coagulator 400 to perform the desired task. Therefore, local control of bipolar coagulator 400 through a user-friendly interface is achieved using a browser in the absence of any communication between bipolar coagulator 400 and local area network 200. Since the present invention user a browser (a web-like interface), the control forms of the device can be changed easily, and can have a variable complexity, as determined by the user's needs. For example, a nurse's display for bipolar coagulator 400 may include buttons that just increase or decrease the power of coagulation, while the surgeon's display may allow selection of different types of current waveforms to fine tune the cutting versus coagulation capabilities of bipolar coagulator 400. To accommodate alternative languages, the evaluation forms stored in ROM simply need to be replaced with forms written in the alternative language.

Figure 4:
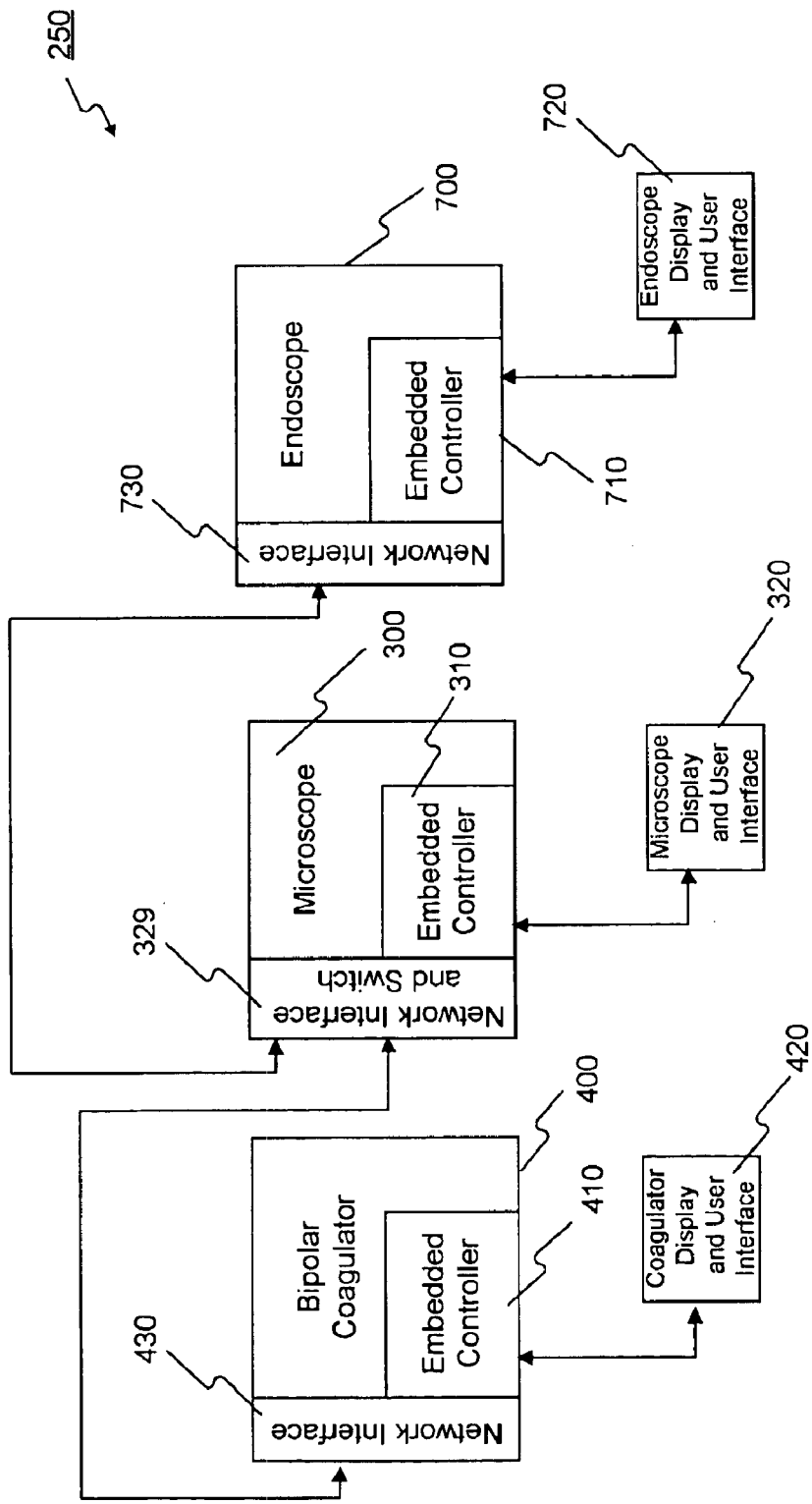
FIG. 4 is a schematic diagram illustrating a second embodiment of the present invention.

The presence of the web-like interface also enables remote control of the device over the network. Since the device can be Jini compliant (i. e., has a Jini compliant embedded controller), in a preferred embodiment, communications within the operating room is established automatically upon connecting the device to the network. The web-like interface allows the device to be controlled by other devices in the operating room. Upon physical connection, the control form in ROM is sent to all other devices in the network to establish control. For example, when the network connects two devices, the display of each device could be selected to display the control form of the other connected device. For example, if microscope 300 is plugged into local area network 200 along with bipolar coagulator 400, the minibrowser of microscope display and user interface 320 will display a list of other control forms available to it over local area network 200. If the user wants to control the connected device, the same form shown locally for that device's local display would also be displayed on the connected device. By pressing the button marked "coagulator," the minibrowser of microscope display and user interface 320 will display the control form for bipolar coagulator 400, and all functions of bipolar coagulator 400 can be manipulated through the control form as displayed on the minibrowser of microscope display and user interface 320. Similarly, as shown in FIG. 4, endoscope 700 has an endoscope display and user interface 720 and a network interface 730 connected to the network interface and switch 329. This bidirectional communication is established simply by plugging the device into network jack switch 128 located in the operating room, as orchestrated by the Jini network protocol and the device's embedded Jini-compliant controller.

According to this embodiment, the functions embedded in the control form are html compliant and can therefore be of virtually any form. Considering microscope 300 as an example, the video signal coming from a camera attached to microscope 300 may be MPEG encoded and placed on the control form. By touching, for example, a "video on" virtual button on the control form of microscope display and user interface 320, the video from the camera would be sent over local area network 200. This embodiment would allow viewing the video from the camera associated with microscope 300 on the display and user interface 420 of bipolar coagulator 400. Similarly, this embodiment contemplates sending video from a navigational device to the projection device within microscope 300. Information from the navigational device could then be viewed as an injected system within the optical axis of microscope 300. Multiple data streams consisting of video, audio, text, and image screens could be sent over the broadband network simultaneously.

Although all of the devices in the operating room, once networked, share a common control mechanism, this embodiment recognizes that the capabilities of each device may vary. For example, bipolar coagulator 400 may have a monochrome display, and would therefore be a poor choice for reviewing a video. Contrarily, microscope 300 may produce multiple video data streams (stereo video in and out) and would therefore have excellent display capabilities within the optical path of microscope 300, and yet embedded controller 310 could intentionally be designed with limited capabilities to control costs.

Certain devices would have no function unless they were networked, such as, for example, a head-mounted video display to view video from a networked endoscope, or a voice recognition unit used to control other devices within the operating room using a program adapted to the surgeon's voice.

Notably, in a networked system of devices according to this embodiment, a single control device, for example a foot switch (not shown) is substituted for the myriad of switches commonly in use today. The single foot switch would be attached to controller 100 and programmed by the surgeon to control specific functions by pressing the switches located within the foot pad with the surgeon's foot. The network infrastructure may also include a robotic device connected to local area network 200, and which may require a complex user interface. Such a complex user interface may preferably be controlled by a device programmed to allow the robot to be controlled according to the surgeon's preferences. In such an embodiment, surgeons could bring their preferences into the operating room by connecting a handheld computer (such as a Palmtop-type unit) containing the surgeon's preferences and downloading the preferences automatically upon connecting the handheld computer to the operating room's network. Additionally, a patient vital sign monitor can be plugged into to network to allow the surgeon to bring in vital signs to his or her display device.

The present invention may employ a wired local-area or wide-area network, or, alternative, may employ a wireless, infrared, or other suitable network, as long as the network has a bandwidth capable of transmitting the appropriate data streams. For a simple device that does not employ video, infrared communication may be adequate. Alternatively, control of a surgical robot would generally require a network that is robust, fast, and resistant to noise, possibly making presently-available wireless networks inappropriate. Further, presently-available wireless networks may allow crosstalk between operating rooms, with the potential for encountering control issues.

Another embodiment of the present invention, however, overcomes crosstalk problems between operating rooms by utilizing the isolation transformer typically provided in operating rooms in addition to a device for introducing a communications signal over existing power grids. One such protocol for introducing communication signals over a power grid is conventionally referred to as the "X10" protocol. The X10 protocol is conventionally used in homes for the purpose of automating various home appliances. Upon coupling an X10 transmitter into a home power grid, for example, all the X 10 receivers plugged into the home power grid receive the communications signal. Upon coupling an X10 transmitter into the power grid of a given operating room, however, the existing isolation transformers ensure that only the other outlets located in the operating room convey the X 10 communications signal associated with that X10 transmitter. Therefore, by introducing a plurality of X10 transmitters into a plurality of operating rooms, the isolation transformers associated with each room ensure that there is a one-to-one mapping of communications signals to operating room power sources. Accordingly, all of the power sources within a single operating room will carry communication signals that bear a known relationship with each other. In this way, a first device plugged into a first power source in an operating room is able to determine which operating room it is plugged into. Furthermore, if a first device is able to communicate with a second device, then by comparing the signals each device access from their respective power sources, the devices are able to determine if they are plugged into the same operating room. Accordingly, one embodiment of the present invention treats the plurality of signals sent over the power grid as a plurality of network data tokens. Furthermore because the signals bear a known relationship to each other in a single operating room, there is a unique network data token associated with that operating room.

Figure 3:
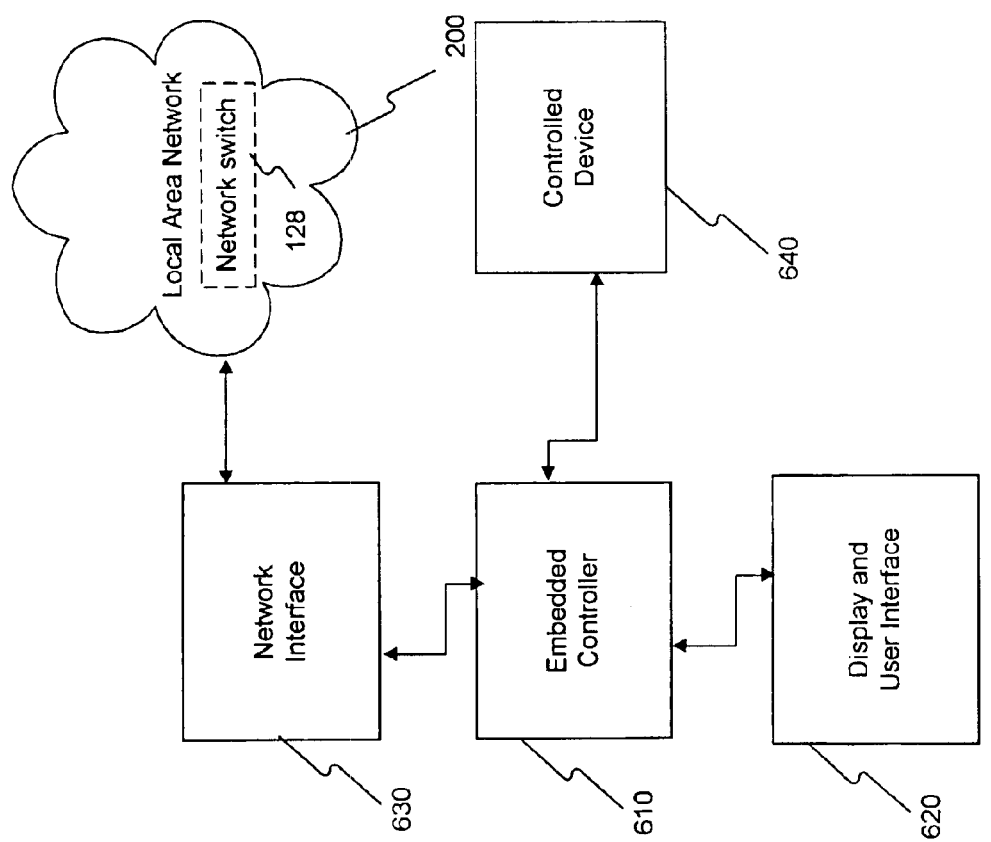
FIG. 3 is a schematic diagram illustrating connection of controlled devices and display devices to the network infrastructure of the present invention as illustrated in FIG. 1.

A general schematic of an exemplary view of the connections depicted in FIG. 1 is shown in FIG. 3. FIG. 3 depicts local area network 200, network switch 128, network interface 630, embedded controller 610, controlled device 640 and display and user interface 620. Network switch 128 can accommodate a plurality of communications channels, and a plurality of devices may be coupled to network switch 128, where each of the plurality of devices has an associated controlled device 640, an embedded controller 610, and a display and user interface 620.

According to the present invention, the network connection would be the only input and output port used for each device. Therefore, the video produced by networked systems, such as microscopes and endoscopes, would be encoded by each device and placed onto the network as a data stream. A display or recording device connected to the network would display or record the data stream, respectively.

Thus, the present invention can use one power supply cable for each device and one network connector for each device. No proprietary cables are needed and minimal expertise is required to establish communication between devices. To activate the device, a user need only roll the device into the operating room, connect the power, connect to the network, and power on the device. In one embodiment of the present invention, the network connection would be physically attached to the power cord, and connection established by plugging in the power cord with the network communications transmitted over the power grid of the hospital. Selection of the network technology is dependent upon the demands placed on the network by the procedures performed within the operating room. If wireless or infrared networks are suitable for the networking needs of particular operating room, no wire is needed, and connecting the power and turning on the device establishes the network. To ensure that only devices within each operating room are connected to each other and not to other devices in the hospital, the combination of the typical isolation transformer with an X10type transmitter and receiver can be used to block extended communications.

FIG. 4 illustrates a further exemplary networking infrastructure 250 according to the present invention. According to this embodiment of the invention, as illustrated in FIG. 4, the plurality of devices (e.g., bipolar coagulator 400, microscope 300, or endoscope 700) each has an embedded controller (e.g., embedded controller 410, embedded controller 310, or embedded controller 710) that is Jini compliant, but the devices are connected to each other rather than through a local-area or wide-area network. In this embodiment, the Jini protocol allows communications to be directly established between two devices without any need for a conventional network. However, almost all procedures require more than two devices, and therefore a device allowing multiple connections is needed. For example, in FIG. 4 an exemplary microscope 300 is provided with multiple connections on network interface and switch 329. If no communication with a network outside of the operating room is desired, then a repeater (not shown) can be used to create the multiple connections when more than two devices are connected.

Figure 5:
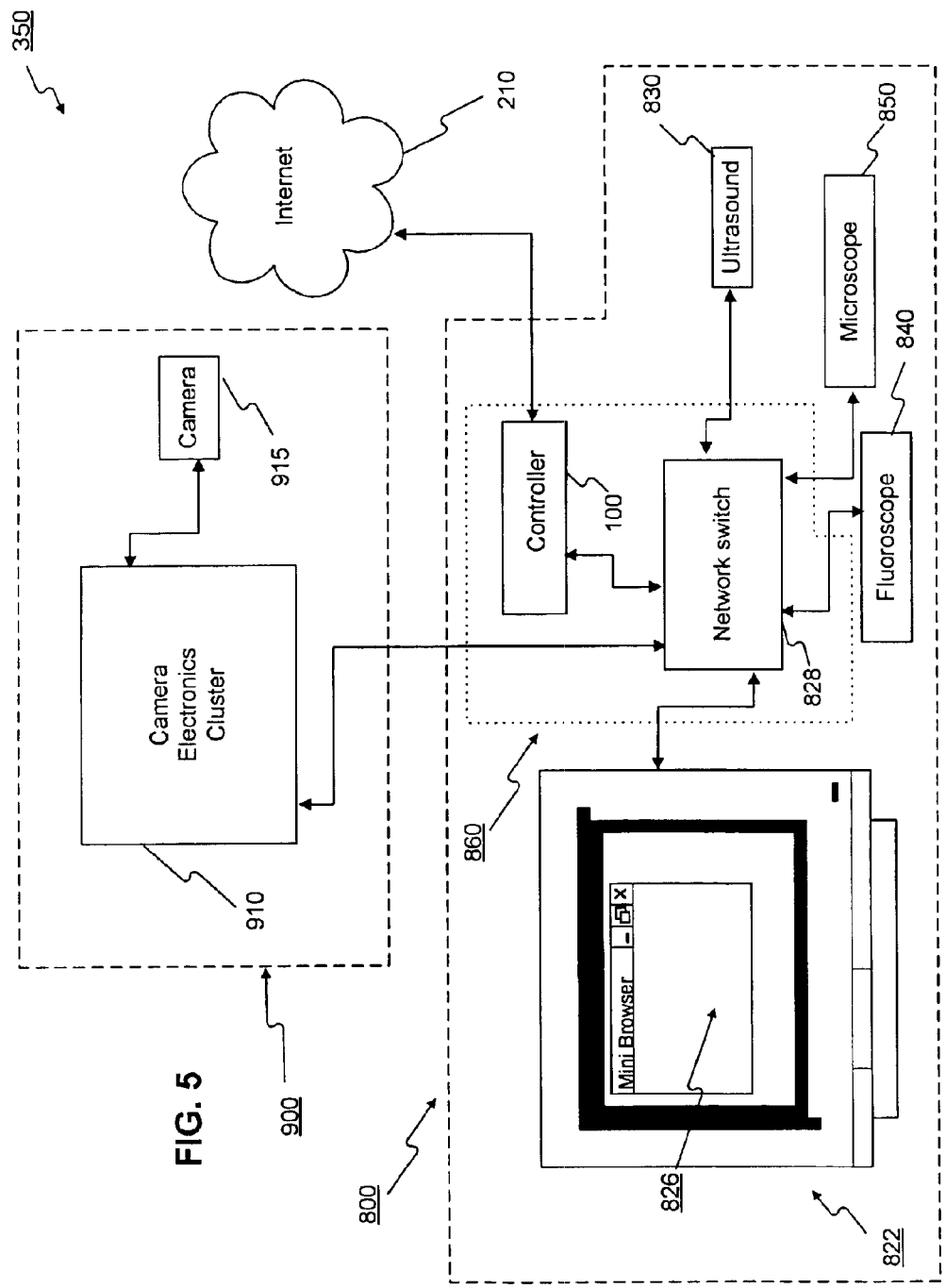
FIG. 5 is a schematic diagram illustrating a third embodiment of the present invention.

Referring to FIG. 5, illustrating another embodiment of the present invention, when communication with an Internet 210 is desired, a networking infrastructure 350 includes network switch 828, such as network jack, which may be wall-mounted. Alternatively, network switch 828 may also be located on a "surgeon's controller," such as controller 100, where the plurality of devices would be plugged into network switch 828 on controller 100. Network switch 828, either on controller 100 or as part of the hospital's networking infrastructure (such as a wall-mounted network jack), assigns to each connected device a network address. This address is dynamically assigned as devices are plugged into and disconnected from network switch 828. Network switch 828 insures that any device physically connected to the network is available for control by all other attached devices. Controller 100 is also responsible for communication between each device and Internet 210.

Communication among the devices and with Internet 210 is controlled by the surgeon or other staff within the operating room using a web-like interface. Thus, the operating room staff has complete control over information allowed into and out of the operating room by the controller, to insure patient privacy and security. For example, if the surgery is being viewed by a group outside of the operating room, the surgeon uses a web-based interface would allow the video stream generated in the operating room to pass to the outside network and be viewable only by the designated address on the Internet. If the surgeon is being assisted by, for example, a remote surgeon onto Internet 210, information could be passed to the remote surgeon, and control of devices within the operating room could be assigned to or shared with the remote surgeon. Such remote information exchange allows the remote surgeon to assist in an endoscopic procedure, for example, by controlling the robotic arm holding the endoscope, and moving the endoscope to show specific areas of interest within the patient. Conversely, the location of the endoscope, as determined by the navigational system, could be shown to the remote surgeon. The remote surgeon would only need a web browser installed on a computer to be able to exert control over the devices in the operating room.

In one implementation of the present invention, certain low level functions are routinely allowed to pass through controller 100. For example, the functional status of a laser is monitored by passing a specific stream of data through network switch 828 and controller 100 to the outside Internet 210. This would allow manufacturers to perform remote testing of their equipment, insure themselves and the hospital that equipment is working properly, and upload improvements in software for specific equipment. Such low level communications can also be used to determine how frequently a device is being used, and how it is performed in the surgical environment. In addition, low level information streams could monitor the quality of surgeon's performance and the appropriateness of the surgery being performed.

The present invention further contemplates use of the network infrastructure with a computer-assisted surgical and diagnostic navigational system, as for example, a STEALTHSTATION (available from Medtronic Sofamor Danek USA, Memphis, Tenn.), and as disclosed in U.S. Pat. Nos. 5,383,454, 5,871,445, 5,891,034 and 5,851,183, and International Publication Nos. WO 94/24933 and WO 96/11624, which are all incorporated herein by reference. A surgical navigation system embodiment of the present invention is illustrated in third networking infrastructure 350 in FIG. 5. In the surgical navigation system embodiment, there are two stand-alone modules: first module 800 and second module 900.

First module 800 comprises a display system 822 having a high resolution touch panel 826 on a pole extending from an electronics cluster located on casters in a preferred embodiment. Network switch 828 is part of display unit 822, along with the computer for a navigational system. A network jack panel is also part of electronics cluster 860, and there is a second network interface with a jack to allow a single connection to Internet 210 through controller 100. A single Internet connection is provided in each operating room, such as in the form of a wall outlet.

Second module 900 in the surgical navigation system embodiment of the present invention provides at least one camera attached to a long arm connected to electronics cluster 910 located on casters. Camera 915 communicates with display system 822 through the network. Therefore, a network cable extends from camera electronics cluster 910 to network switch 828 in the first module 800, and another cable extends from display system 822 to the wall jack connected to Internet 210. Any other devices used with the network are connected to network switch 828 located in electronics cluster 860. Thus, display system 822 and electronics cluster 860 is the hub of the operating room network. Alternatively, network switch 828 can be wall-mounted in the operating room so that the surgical navigation system need not contain network switch 828.

Notably, any new technology can be incorporated easily into the system by making the new technology Jini compliant. For example, a robot can be controlled by the networked system if its control mechanisms were programmed to accept the web interface standard. New display or control devices, ultrasound devices 830, fluoroscopes 840, or microscope 850 can connect to the network and transmit their images, and be controlled by other devices within the operating room. In this way, the network infrastructure of the present invention makes the surgical navigation system compatible with all foreseeable technological innovations, and fosters development of new technologies without need for reprogramming for each device. Further, any device can be brought into an existing operating room without reprogramming the existing units, as all forms needed to control a specific device are contained in the ROM of that device.

II. CONCLUSION

Systems consistent with the present invention form a networking infrastructure for an operating room. Systems consistent with the present invention also have utility in many areas where different electronic devices benefit from being interconnected. The foregoing description of an implementation of the invention has been presented for purposes of illustration and description. It is not exhaustive and does not limit the invention to the precise form disclosed. Modifications and variants are possible in light of the above teachings or may be acquired from practicing the invention. For example, FIGS. 1 and 3 depict a local area network as the network associated with an operating room. However, the network associated with the operating room may be any type of network known in the art, as for example, a wide-area network or Intranet. Furthermore, although some of the connections between the devices were described as cables, such connections may be wireless, infrared, or any other suitable network known in the art. Still further, the preferred embodiments recited the use of embedded controllers that are Jini-compliant. However, again, any such equivalent conventional specifications as are known in the art may be used. Accordingly, the invention is not limited to the above described embodiments, but instead is defined by the appended claims in light of their full scope of equivalents.

What is claimed is:

1. A networking infrastructure comprising:

a network switch;

a first device, coupled to said network switch through a first communication channel; and a second device, coupled to said network switch through a second communications channel; wherein said first device comprises:
  a first controlled device;
  a first display and user interface; and
  a first controller, responsive to said first display and user interface, said first controller controlling said first controlled device, said first controlled device responsive only to said first controller;
and wherein said second device comprises:
  a second controlled device;
  a second display and user interface; and
  a second controller, responsive to said second display and user interface, said second controller controlling said second controlled device, said second controlled device responsive only to said second controller; and
  wherein said second controller controls said first controlled device in response to said second display and user interface by interaction between said first controller and said second controller via said first communications channel, said second communications channel, and said network switch.

2. A networking infrastructure comprising:

a network switch;

a first device, coupled to said network switch through a first communications channel; and a second device, coupled to said network switch through a second communications channel; wherein said first device comprises:
  a first controlled device;
  a first display and user interface; and
  a first controller, responsive to said first display and user interface, said first controller controlling said first controlled device, and first controlled device responsive only to said first controller;
and wherein said second device comprises:
  a second controlled device; and
  a second controller controlling said second controlled device, said second controlled device responsive only to said second controller; and
  wherein said first controller controls said second controlled device in response to said first display and user interface by interaction between said first controller and said second controller via said first communications channel, said second communications channel, and said network switch.

3. The networking infrastructure of claim 1 or 2, wherein said network switch, said first device, and said second device are used in a controlled-access environment.

4. The networking infrastructure of claim 3, wherein said controlled-access environment is an operating room.

5. The networking infrastructure of claim 3, further comprising:

a master controller;

a first data stream, influenced by said first controlled device; and an external processor, coupled to said network switch through said master controller and configured to determine said influence of said first controlled device on said first data stream; wherein said master controller is configured to isolate said first data stream from said external processor.

6. The networking infrastructure of claim 3, further comprising:

a master controller;

a first data stream influenced by said first controlled device; and an external processor, coupled to said network switch through said master controller, and configured to determine said influence of said first controlled device on said first data stream; wherein said master controller is configured to allow said external processor access to said first data stream.

7. The networking infrastructure of claim 3, further comprising:
a switch;
wherein said switch is configured to permit control of said first controlled device and said second controlled device.

8. The networking infrastructure of claim 3 wherein said first controlled device is a surgical navigation system.

9. The networking infrastructure of claim 3, wherein said first device is further configured to store a first control form; and wherein said first display and user interface is configured to display said first control form; and
wherein said second device is further configured to store a second control form; and wherein said second display and user interface is configured to display said second control form.

10. The networking infrastructure of claim 9, wherein said first display and user interface is further configured to display said first control form in a browser interface.

11. The networking infrastructure of claim 9, wherein said second display and user interface is configured to access and allow display of said first control form upon coupling with said network switch.

12. A networking infrastructure comprising:
a first network token, accessible over a first power source;
a second network token, accessible over a second power source;
a first device, coupled to a first network switch through a first communications channel, and configured to access said first network token upon connection to first power source; and
a second device, coupled to a second network switch through a second communications channel, and configured to access said second network token upon connection to said second power source;
wherein said first device comprises:
a first controlled device;
a first display and user interface; and
a first controller, responsive to said first display and user interface, said first controller controlling said first controlled device, said first controlled device responsive only to said first controller; and
wherein said second device comprises:
a second controller device;
a second display and user interface; and
a second controller, responsive to said second display and user interface, said second controller controlling said second controlled device, said second controlled device responsive only to said second controller; and
wherein said second controller controls said first controlled device in response to said second display and user interface by interaction between said first controller and said second controller only if said first network token matches said second network token.

13. A networking infrastructure comprising:
a first network token, accessible over a first power source;
a second network token, accessible over a second power source;
a first device, coupled to a first network switch through a first communication channel, and configured to access said first network token upon connection to first power source; and
a second device, coupled to a second network switch through a second communications channel, and configured to access said second network token upon connection to said second power source;
wherein said first device comprises:
a first controlled device;
a first display and user interface; and
a first controller, responsive to said first display and user interface, said first controller controlling said first controlled device, said first controlled device responsive only to said first controller; and
wherein said second device comprises:
a second controlled device; and
a second controller controlling said second controlled device, said second controlled device responsive only to said second controller; and
wherein said first controller controls said second controlled device in responsive to said first display and user interface by interaction between said first controller and said second controller only if said first network token matches said second network token.

14. The networking infrastructure of claims 12 or 13, wherein said first device, said second device, and said first network switch are used in a controlled access environment.

15. The networking infrastructure of claim 14, wherein said controlled-access environment is an operating room.

16. The networking infrastructure of claim 14 wherein said first power source and said second power source are further coupled to at least one X10-type transmitter configured to introduced a first communications signal; wherein said first power source and second power source are further coupled to at least one isolation transformer; and wherein said first network token is derived from said first communications signal.

17. A networking infrastructure comprising:
a first device;
a second device, coupled to said first device through a first communications channel; and
a third device, coupled to said first device through a second communications channel, and coupled to said second device through said second communications channel and said first communications channel;
wherein said first device comprises:
a first controlled device;
a first display and user interface; and
a first controller, responsive to and first display and user interface, said first controller controlling said first controlled device, said first controlled device responsive only to said first controller; and
wherein said second device comprises:
a second controlled device; and
a second controller, controlling said second controller device, said second controlled device responsive only to said second controller, wherein said first controller controls the second controlled device in response to said first display and user interface by interaction between said first controller and said second controller via said first communications channel and said second communications channel; and
wherein said third device comprises:
a third controlled device; and
a third controller, controlling said third controlled device, said third controlled device responsive only to said third controller, wherein said first controller controls the third controlled device in response to said first display and user interface by interaction between said first controller and third controller via said first communications channel and said second communications channel.

18. The networking infrastructure of claim 17, wherein said first device, said second device, and said third device are used in a controlled-access environment.

19. The networking infrastructure of claim 18, wherein said controlled-access environment is an operating room.

20. A networking infrastructure comprising:
- a first network token accessible over a first power source, wherein said first power source is coupled to at least one X10-type transmitter configured to introduce a first communications signal and is coupled to at least one isolation transformer, and wherein said first network token is derived from the first communications signal;
- a second network token accessible over a second power source, wherein said second power source is coupled to at least one X10-type transmitter configured to introduce a second communications signal and is coupled to at least one isolation transformer, and wherein said second network token is derived from the second communications signal;
- a first device, coupled to a first network switch through a first communications channel, and configured to access said first network token upon connection to first power source; and
- a second device, coupled to a second network switch through a second communications channel, and configured to access said second network token upon connection to second power source;
- wherein said first device comprises:
  - a first controlled device;
  - a first display and user interface; and
  - a first controller, configured to permit control of said first controlled device through said first display and user interface; and
- wherein said second device comprises:
  - a second controlled device;
  - a second display and user interface; and
  - a second controller; and
- wherein said first controller and second controller are further configured to permit control of said second controlled device through said first display and user interface only if said first network token matches said second network token.

21. A networking infrastructure comprising:
- a first network token accessible over a first power source, wherein said first power source is coupled to at least one X10-type transmitter configured to introduce a first communications signal and is coupled to at least one isolation transformer, and wherein said first network token is derived from the first communications signal;
- a second network token accessible over a second power source, wherein said second power source is coupled to at least one X10-type transmitter configured to introduce a second communications signal and is coupled to at least one isolation transformer, and wherein said second network token is derived from the second communications signal
- a first device, coupled to a first network switch through a first communications channel, and configured to access said first network token upon connection to first power source; and
- a second device, coupled to a second network switch through a second communications channel, and configured to access said second network token upon connection to said second power source;
- wherein said first device comprises:
  - a first controlled device;
  - a first display and user interface; and
  - a first controller, configured to permit control of said first controlled device through said first display and user interface; and
- wherein said second device comprises:
  - a second controlled device; and
  - a second controller; and
- wherein said first controller and said second controller are further configured to permit control of said second controlled device through said first display and user interface only if said first network token matches said second network token.

* * * * *